United States Patent
Bellar

(10) Patent No.: US 10,918,651 B2
(45) Date of Patent: Feb. 16, 2021

(54) METHOD FOR LOWERING THYROTROPIN LEVELS IN ADULTS

(71) Applicant: University of Louisiana at Lafayette, Lafayette, LA (US)

(72) Inventor: David Bellar, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 0 days.

(21) Appl. No.: 15/704,482

(22) Filed: Sep. 14, 2017

(65) Prior Publication Data

US 2018/0078571 A1    Mar. 22, 2018

Related U.S. Application Data

(60) Provisional application No. 62/395,399, filed on Sep. 16, 2016.

(51) Int. Cl.
*A61K 31/685* (2006.01)

(52) U.S. Cl.
CPC ................. *A61K 31/685* (2013.01)

(58) Field of Classification Search
CPC .................................................. A61K 31/685
See application file for complete search history.

(56) References Cited

PUBLICATIONS

Moreno (Clinical Therapeutics vol. 25, Issue 1, Jan. 2003, pp. 178-193) . (Year: 2003).*
Aan Het Rot et al. ("Neurobiological mechanisms in major depressive disorder," CMAJ. Feb. 3, 2009; 180(3): 305-313). (Year: 2009).*
Estrada et al. ("Thyrotropin Isoforms: Implications for Thyrotropin Analysis and Clinical Practice," Thyroid. Mar. 1, 2014; 24(3): 411-423). (Year: 2014).*
Cavun and Savci, "CDP-choline increases plasma ACTH and potentiates the stimulated release of GH, TSH and LH: the cholinergic involvement," Fundam Clin Pharmacol. Oct. 2004;18(5):513-23. (Year: 2004).*

* cited by examiner

*Primary Examiner* — Kortney L. Klinkel
*Assistant Examiner* — William Y Lee
(74) *Attorney, Agent, or Firm* — Jessica C. Engler; Russel O. Primeaux; Kean Miller LLP

(57) ABSTRACT

The inventor has discovered that a particular dosage of Alpha Glycerylphosphoryl Choline administered to adult males results in a reduction of thyrotropin serum. Thytotropin levels are depressed with increased dopamine levels in the brain, and CDP-choline has been shown to increase dopamine and dopamine receptor density in the CNS. By suppressing the TSH levels in the brain to increase dopamine levels, this invention can assist in the treatment of depression, as well as symptoms of hyperthyroidism such as chills, depression, sluggishness, or feelings of weakness.

4 Claims, 1 Drawing Sheet

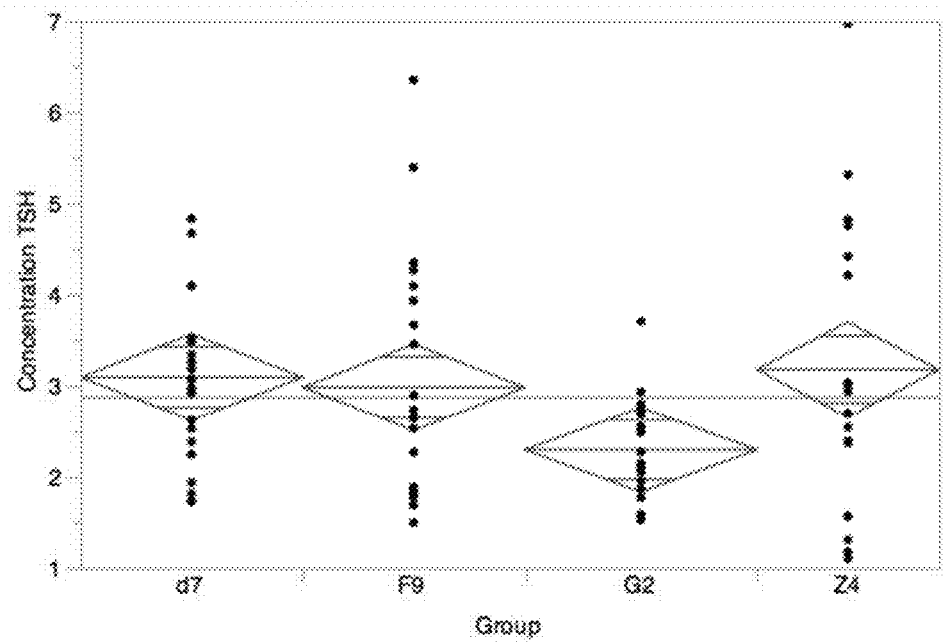

METHOD FOR LOWERING THYROTROPIN LEVELS IN ADULTS

CROSS REFERENCE TO RELATED APPLICATION

This application claims priority to and the benefit of U.S. Provisional Patent Application Ser. No. 62/395,399, filed on Sep. 16, 2016, titled "Alpha Glycerylphosphoryl Choline Effects Neurotransmitter Levels and Thyroid Stimulating Hormone".

STATEMENT REGARDING FEDERALLY SPONSORED RESEARCH OR DEVELOPMENT

Not applicable.

REFERENCE TO A "SEQUENCE LISTING", A TABLE, OR COMPUTER PROGRAM

Not applicable.

DESCRIPTION OF THE DRAWINGS

The drawings constitute a part of this specification and include exemplary examples of the ALPHA GLYCERLPHOSPHORYL CHOLINE EFFECTS NEUROTRANSMITTER LEVELS AND THYROID STIMULATIN HORMONE, which may take the form of multiple embodiments. It is to be understood that in some instances, various aspects of the invention may be shown exaggerated or enlarged to facilitate an understanding of the invention. Therefore, drawings may not be to scale.

FIG. 1 depicts the results of testing of this invention.

FIELD OF THE INVENTION

This invention generally relates to the field of hormones and the effect that chemically impacting said hormones can have on the human body. Specifically, this invention is related to using Alpha Glycerylphosphoryl Choline in order to lower the levels of thyroid stimulating hormone.

BACKGROUND OF THE INVENTION

Thyroid stimulating hormone is secreted by the pituitary gland that regulates the production of thyroid hormones. It is known in the art that dopamine is a regulator of thyroid stimulating hormone ("TSH"). Scanlon et al., *Dopamine is a physiological regulator of thyrotrophin (TSH) secretion in normal men*, Clin Endorcrinol (Oxf). 1979, 10(1): 7-15; de Zegher et al., *Dopamine suppresses thyroid-stimulating hormone secretion in neonatal hypothyroidism*, Acta Paediatr. 1995, 84(2): 213-214. Substances that can cross the blood brain barrier and effect neurotransmitter levels many cause changes in circulating TSH.

Alpha Glycerylphosphoryl Choline ("A-GPC") is a substance that is capable of crossing the blood brain barrier and has been shown to be incorporated into brain phospholipids within twenty-four hours of administration. Parnetti et al., *Cholinergic precursors in the treatment of cognitive impairment of vascular origin: Ineffective approaches or need for re-evaluation?*, Journal of Neurological Sciences, 2007, 257: 264-269. In previous studies, CDP-choline (a cholinergic precursor) has also been shown to increase dopamine receptors in the brain with chronic administration. Giménez R, Raïch J and Aguilar J., *Changes in brain striatum dopamine and acetylcholine receptors induced by chronic CDP-choline treatment of aging mice*, Br J Pharmacol. 1991, 104(3): 575-578. Dopamine receptors are responsive to dopamine levels in the CNS and to dopaminergic treatments. Thobois et al., *Role of dopaminergic treatment in dopamine receptor down regulation in advanced Parkinson disease: a positron emission tomographic study*, Arch Neurol. 2004, 61:1705-1709. CNS dopamine is involved in reward behavior, motor control and additionally controls the release of several other hormones. However, to determine changes in dopamine with acute treatment of a cholinergic precursor, monitoring TSH in the serum could signal changes associated with dopamine.

SUMMARY OF THE INVENTION

Based on the evaluation of a study conducted by the inventor, TSH blood levels in healthy adults can be reduced through the administration of 500 mg of A-GPC. Due to these results, administration of A-GPC at this level may provide an effective means to treat depression and symptoms of hypothyroidism.

DETAILED DESCRIPTION OF THE INVENTION

This inventor has determined that administration of 500 mg of A-GPC reduces the TSH blood levels healthy adults. It has also been noted that as singe administration of 250 mg was found insufficient to reduce blood TSH. Thus given the known ability of A-GPC to cross the blood brain barrier, this invention provides an effective means to therapeutically suppress the TSH blood levels. Suppression of TSH levels can assist in the treatment of depression, as well as symptoms of hyperthyroidism such as chills, depression, sluggishness, or feelings of weakness. Previous research has shown A-GPC to be effective at a treatment for vascular dementia, however, no research on A-GPC has examined systems related to dopamine, nor have any nutrition experts suggested a role for A-GPC in modifying dopamine or TSH levels. In practice A-GPC has previously only been known to increase Acetyl Choline levels in the central nervous system. This invention expands the understanding of A-GPC in a novel way, unrelated to previous knowledge and regarding distinctly different functions in the central nervous system.

A study was performed of this invention using forty-eight male college-aged volunteers. The participants were divided into 4 groups of 12 subjects. The groups reported to the lab after an overnight fast and were then administered the following: 200 mg of Caffeine, 250 mg of A-GPC, 500 mg of A-GPC or placebo. One hour and two hours post administration blood was drawn from a vein in the antecubital space into a serum separator tube, this was allowed to stand for 15 minutes, then centrifuged and the serum drawn off and frozen at −35 degrees Celsius for later evaluation.

At the conclusion of data collection, the serum aliquots were thawed and a commercially available high-sensitivity ELISA was uses to quantify TSH levels (Eagle Biosciences TSH Ultrasensitive ELISA kit). Samples were tested in duplicate with inter and intra place CV % of less than 10. A repeated measures Anova was used to assess TSH level by group. Main effects for time (1 hour, 2 hour) were not noted in the analysis. The results of the analysis are shown in FIG. 1. As seen in this analysis, the group who received 500 mg of A-GPC (G2) demonstrated significantly lower TSH levels as compared to all other groups in the study.

It has been suggested in prior works that TSH levels in young men of 2.0 may be abnormal, thus with a group average of 2.3 and with 5 of the 12 males exhibiting levels lower than 2.0, this invention finds that a 500 mg dose of A-GPC results in significantly suppressed TSH blood levels.

The described features, advantages, and characteristics may be combined in any suitable manner in one or more embodiments. One skilled in the relevant art will recognize that the various components of this design may be practiced without one or more of the specific features or advantages of a particular embodiment. In other instances, additional features and advantages may be recognized in certain embodiments that may not be present in all embodiments.

Reference throughout this specification to "one embodiment", "an embodiment", or similar language means that a particular feature, structure, or characteristic described in connection with the embodiment is included in at least one embodiment. Thus the appearance of the phrase "in one embodiment", "in an embodiment", and similar language throughout this specification may, but do not necessarily, all refer to the same embodiment.

I claim:

1. A method for reducing thyroid stimulating hormone levels in adults by administering Alpha Glycerylphosphoryl Choline to said adult.

2. The method of claim 1, wherein prior to receiving said Alpha Glycerylphosphoryl Choline, the adult fasted for a minimum of eight hours.

3. The method of claim 1, wherein said Alpha Glycerylphosphoryl Choline was administered at a dose greater than 250 mg.

4. The method of claim 1, wherein said Alpha Glycerylphosphoryl Choline was administered at a dose of 500 mg.

\* \* \* \* \*